United States Patent [19]

Noda et al.

[11] Patent Number: 5,856,557

[45] Date of Patent: Jan. 5, 1999

[54] PROCESS FOR PRODUCING HEXAFLUOROBIPHENYL -3,3',4,4'-TETRACARBOXYLIC ACID PRECURSORS

[75] Inventors: Yumiki Noda, Ichihara; Takashi Honma, Ube, both of Japan

[73] Assignee: Ube Industries, Ltd., Ube, Japan

[21] Appl. No.: 873,767

[22] Filed: Jun. 12, 1997

[30] Foreign Application Priority Data

Jun. 14, 1996 [JP] Japan ................................. 8-153750

[51] Int. Cl.$^6$ .................................................. C07C 255/50
[52] U.S. Cl. ......................... 558/360; 560/83; 560/102; 558/378; 558/425
[58] Field of Search ................... 560/83, 102; 558/360, 558/378, 425

[56] References Cited

U.S. PATENT DOCUMENTS 3,440,277   4/1969   Holland et al. .

FOREIGN PATENT DOCUMENTS 3-101673   4/1991   Japan .

OTHER PUBLICATIONS

Birchall, J Chem Soc C "Polyfluoroarenes" pp. 1343–1348, 1971.

CA:115:583075 abs of JP03101673, Apr. 1991.

Primary Examiner—Paul J. Killos
Assistant Examiner—Jean F. Vollano
Attorney, Agent, or Firm—Finnegan, Henderson, Farabow, Garrett & Dunner, L.L.P.

[57] ABSTRACT

A 2,2',5,5',6,6'-hexafluorobiphenyl-3,3',4,4'-tetracarboxylic acid precursor as an intermediate material for a highly functional fluororesin may be produced at a high yield by reacting tetrafluorophthalonitrile with an alkali metal iodide.

6 Claims, No Drawings

PROCESS FOR PRODUCING HEXAFLUOROBIPHENYL -3,3',4,4'- TETRACARBOXYLIC ACID PRECURSORS

BACKGROUND OF THE INVENTION

1. Field of the Invention

The present invention relates to a process for producing 2,2',5,5',6,6'-hexafluorobiphenyl-3,3',4,4'-tetracarboxylic acid precursors which are useful as intermediate materials for highly functional fluororesins with excellent heat resistance, light resistance, low moisture absorption and low permittivity.

2. Description of the Related Art

Recent years have seen an increased demand for resins with high functionality. Functional materials having high heat resistance, low moisture absorption and low permittivity have been particularly desired in the electronics industry.

Fluorinated polyimides are examples of materials which can meet this demand, and fluorinated tetracarboxylic dianhydrides are known as aromatic tetracarboxylic acid components thereof.

Among these there is known 2,2',5,5',6,6'-hexafluorobiphenyl-3,3',4,4'-tetracarboxylic dianhydride, represented by the following formula (4).

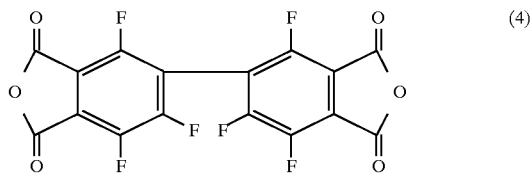

This 2,2',5,5',6,6'-hexafluorobiphenyl-3,3',4,4'-tetracarboxylic dianhydride is usually produced by anhydrating 2,2',5,5',6,6'-hexafluorobiphenyl-3,3',4,4'-tetracarboxylic acid.

Only two types of processes are known for their synthesis. One is the process described in U.S. Pat. No. 3,440,277 (1969). This patent specification gives examples of producing 2,2',5,5',6,6'-hexafluorobiphenyl-3,3',4,4'-tetracarboxylic acid, 2,2',5,5',6,6'-hexafluorobiphenyl-3,3',4,4'-tetracarboxylic acid tetramethyl ester and 2,2',5,5',6,6'-hexafluorobiphenyl-3,3',4,4'-tetracarboxylic dianhydride. However, the process described in this patent specification is a synthesis process requiring multiple stages employing a polyfluoroaromatic lithium compound during the synthesis, and because this compound necessitates special care for handling and increases costs, this process has been disadvantageous for industrial production.

The other process is described in Japanese Unexamined Patent Publication No. 3-101673. This process uses 4-bromo-3,5,6-trifluorophthalonitrile and copper powder to synthesize 3,3',5,5',6,6'-hexafluoro-4,4'-biphthalonitrile by the Ullmann reaction. The same publication also describes hydrolysis and anhydration of the 3,3',5,5',6,6'-hexafluoro-4,4'-biphthalonitrile to obtain 3,3',5,5',6,6'-hexafluoro-4,4'-biphthalic dianhydride in an approximately quantitative manner.

This process requires a large excess of copper in the production step for the 3,3',5,5',6,6'-hexafluoro-4,4'-biphthalonitrile (2,2',5,5',6,6'-hexafluorobiphenyl-3,3',4,4'-tetracarbonitrile) and, with a yield as low as about 18%, it is not satisfactory as an industrial production process.

In summary, to date there has been no industrially practical production process for high-yield production of 2,2',5,5',6,6'-hexafluorobiphenyl-3,3',4,4'-tetracarboxylic acid precursors such as 2,2',5,5',6,6'-hexafluorobiphenyl-3,3',4,4'-tetracarbonitrile and 2,2',5,5',6,6'-hexafluorobiphenyl-3,3',4,4'-tetracarboxylic tetraalkyl esters, which are useful as synthetic intermediates for 2,2',5,5',6,6'-hexafluorobiphenyl-3,3',4,4'-tetracarboxylic dianhydride.

SUMMARY OF THE INVENTION

The present invention provides an industrially practical production process for high-yield production of 2,2',5,5',6,6'-hexafluorobiphenyl-3,3',4,4'-tetracarboxylic acid precursors which are useful as synthetic intermediates for 2,2',5,5',6,6'-hexafluorobiphenyl-3,3',4,4'-tetracarboxylic dianhydride.

The present invention provides a process for producing a 2,2',5,5',6,6'-hexafluorobiphenyl-3,3',4,4'-tetracarboxylic acid precursor represented by the following general formula (3)

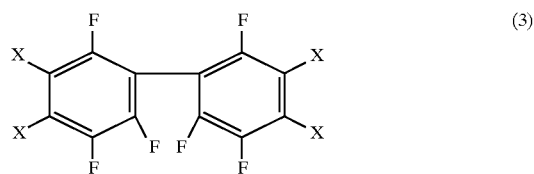

wherein X represents CN or COOR, R representing an alkyl group of 1–5 carbon atoms, which comprises reacting a tetrafluorobenzene-o-dicarboxylic acid precursor represented by the following general formula (1)

wherein X represents CN or COOR, R representing an alkyl group of 1–5 carbon atoms, and an alkali metal iodide represented by the following general formula (2)

wherein M represents an alkali metal, in a polar solvent.

DESCRIPTION OF THE PREFERRED EMBODIMENTS

The above-mentioned tetrafluorobenzene-o-dicarboxylic acid precursor may be tetrafluorobenzene-o-dicarbonitrile, tetrafluorobenzene-o-dicarboxylic acid dimethyl ester, tetrafluorobenzene-o-dicarboxylic acid diethyl ester, tetrafluorobenzene-o-dicarboxylic acid dipropyl ester, tetrafluorobenzene-o-dicarboxylic acid dibutyl ester, etc.

These compounds are publicly known and can be purchased, for example, from Fluorochem Co. (England), Tokyo Chemicals, KK. (Japan) and Aldrich Co. (U.S.A.).

According to the invention it is important that the aforementioned tetrafluorobenzene-o-dicarboxylic acid precursor is reacted with the alkali metal iodide, and this quite unexpectedly promotes a coupling reaction whereby the 2,2',5,5',6,6'-hexafluorobiphenyl-3,3',4,4'-tetracarboxylic acid precursor is obtained substantially without producing any positional isomers.

The aforementioned alkali metal iodide may be lithium iodide, sodium iodide, potassium iodide, rubidium iodide, cesium iodide, etc., with sodium iodide and potassium iodide being preferred from the standpoint of reactivity and economy. The amount of the alkali metal iodide to be used is preferably about 0.5–2 moles, and especially 0.9–1.5 moles with respect to one mole of the tetrafluorobenzene-o-dicarboxylic acid precursor. Use in an amount outside of this range results in a notably lower yield of the 2,2',5,5',6,6'-hexafluorobiphenyl-3,3',4,4'-tetracarboxylic acid precursor.

Any of a variety of solvents may be used as the aforementioned polar solvent, among which may be mentioned dimethylformamide, dimethylacetamide, dimethylsulfoxide, N-methylpyrrolidone, hexamethylphosphoric triamide and 1,3-dimethyl-2-imidazolidinone because of their reactivity and solubility, with dimethylformamide being preferred. The amount of the polar solvent to be used is preferably about 100–10,000 ml, and especially 300–5000 ml to one mole of the tetrafluorobenzene-o-dicarboxylic acid precursor.

The reaction temperature is an appropriate temperature in a range of from at least 70° C. to not higher than the boiling point of the solvent used, and preferably about 100°–150° C. If the temperature is too low the conversion rate of the tetrafluorobenzene-o-dicarboxylic acid precursor is low, and if the temperature is too high the yield of the 2,2',5,5',6,6'-hexafluorobiphenyl-3,3',4,4'-tetracarboxylic acid precursor is low. The reaction time is about 0.1 to 15 hours, and preferably about 0.5–8 hours. The reaction system is preferably purged with an inert gas such as nitrogen.

After the reaction, the 2,2',5,5',6,6'-hexafluorobiphenyl-3,3',4,4'-tetracarboxylic acid precursor is obtained using column chromatography or by recrystallization with an aromatic hydrocarbon solvent or alcohol.

The 2,2',5,5',6,6'-hexafluorobiphenyl-3,3',4,4'-tetracarboxylic acid precursor obtained by this process, such as 2,2',5,5',6,6'-hexafluorobiphenyl-3,3',4,4'-tetracarbonitrile, may be used as an synthetic intermediate for 2,2',5,5',6,6'-hexafluorobiphenyl-3,3',4,4'-tetracarboxylic dianhydride. The conversion from the 2,2",5,5',6,6'-hexafluorobiphenyl-3,3',4,4'-tetracarbonitrile to 2,2',5,5',6,6'-hexafluoro-3,3',4,4'-biphthalic dianhydride by way of 2,2',5,5',6,6'-hexafluorobiphenyl-3,3',4,4'-tetracarboxylic acid may be accomplished by hydrolysis and anhydration according to common methods.

The present invention will now be explained in more detail by way of the following non-limitative examples.

EXAMPLE 1

After loading 5.0 g (25.0 mmol) of tetrafluorobenzene-o-dicarbonitrile (melting point: 86° C., Fluorochem Co.) and 4.15 g (25.0 mmol) of potassium iodide into a 100 ml 3-necked flask equipped with a reflux condenser tube, the interior of the flask was exchanged with nitrogen. To this was added 35 ml of dimethylformamide prior to reaction at 140° C. for 3 hours. Upon analysis of the reaction solution by gas chromatography (OV17 column, product of Shimazu Laboratories), 2,2',5,5',6,6'-hexafluorobiphenyl-3,3',4,4'-tetracarbonitrile was found to be produced with a tetrafluorobenzene-o-dicarbonitrile conversion rate of 63% and 83% selectivity.

After cooling the reaction mixture to room temperature, 150 ml of ethyl acetate was added and the solution was washed with a 3% aqueous hydrochloric acid solution and then with a 10% aqueous sodium thiosulfate solution. After distilling off the ethyl acetate, the residue was purified by column chromatography (silica gel/toluene:hexane=7:3) to obtain 2.10 g of 2,2',5,5',6,6'-hexafluorobiphenyl-3,3',4,4'-tetracarbonitrile. The yield was 46%.

The product analysis values were as follows.
MS measurement, M$^+$: 362
$^{19}$FNMR measurement (400 MHz, standard substance: CF$_3$COOH— 76.5 ppm, solvent: DMSO$_{d6}$)
  δ=−104.60 (2F)
  −117.850–117.907 (2F)
  −129.069–129.119 (2F)

EXAMPLE 2

A reaction was conducted under the same conditions as in Example 1 except that sodium iodide was used instead of potassium iodide. Upon analysis by gas chromatography after the reaction, 2,2',5,5',6,6'-hexafluorobiphenyl-3,3',4,4'-tetracarbonitrile was found to be obtained with a tetrafluorobenzene-o-dicarbonitrile conversion rate of 53% and 51% selectivity.

EXAMPLE 3

The same reaction as Example 1 was conducted under the same conditions except that dimethylsulfoxide was used as the solvent. Upon analysis by gas chromatography after the reaction, 2,2',5,5',6,6'-hexafluorobiphenyl-3,3',4,4'-tetracarbonitrile was found to be obtained with a tetrafluorobenzene-o-dicarbonitrile conversion rate of 35% and 42% selectivity.

According to the present invention, it is possible to produce 2,2',5,5',6,6'-hexafluorobiphenyl-3,3',4,4'-tetracarboxylic acid precursors, such as 2,2',5,5',6,6'-hexafluorobiphenyl-3,3',4,4'-tetracarbonitrile, which are useful as intermediate materials for highly functional fluororesins, at a high yield by an industrially practical and simple process.

We claim:

1. A process for producing a 2,2',5,5',6,6'-hexaflurobiphenyl-3,3',4,4'-tetracarboxylic acid precursor represented by the following general formula (3)

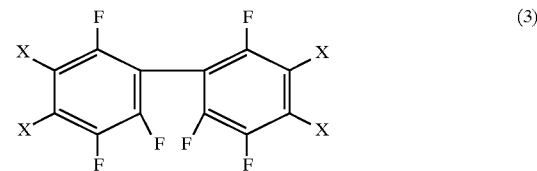

wherein X represents CN or COOR and R represents an alkyl group of 1–5 carbon atoms, which comprises reacting a tetrafluorobenzene-o-dicarboxylic acid precursor represented by the following general formula (1)

wherein X represents CN or COOR and R represents an alkyl group of 1–5 carbon atoms with potassium iodide in dimethylformamide.

2. The process of claim 1, wherein said tetrafluorobenzene-o-dicarboxylic acid precursor represented by the general formula (1) is selected from the group consisting of tetrafluorobenzene-o-dicarbonitrile, tetrafluorobenzene-o-dicarboxylic acid dimethyl ester, tetrafluorobenzene-o-dicarboxylic acid diethyl ester, tetrafluorobenzene-o-dicarboxylic acid dipropyl ester, and tetrafluorobenzene-o-dicarboxylic acid dibutyl ester.

3. The process of claim 1, wherein the amount of said potassium iodide is about 0.5–2 moles to one mole of said tetrafluorobenzene-o-dicarboxylic acid precursor.

4. The process of claim 1, wherein the amount of said dimethylformamide is 100–10,000 ml to one mole of said tetrafluorobenzene-o-dicarboxylic acid precursor.

5. The process of claim 1, wherein the reaction is conducted at a temperature of 100°–150° C.

6. The process of claim 1, wherein reaction time is from about 0.1 to 15 hours.

* * * * *